(12) United States Patent
Görtz et al.

(10) Patent No.: US 7,064,177 B2
(45) Date of Patent: Jun. 20, 2006

(54) PRODUCTION OF POLYOXYMETHYLENE AND SUITABLE (II) CATALYSTS

(75) Inventors: Hans-Helmut Görtz, Freinsheim (DE); Gerrit Luinstra, Mannheim (DE); Wolfram Wielandt, Tübingen (DE); Michael Henes, Jettenburg (DE); Ekkehard Lindner, Tübingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/510,477

(22) PCT Filed: Apr. 10, 2003

(86) PCT No.: PCT/EP03/03745

§ 371 (c)(1),
(2), (4) Date: Oct. 7, 2004

(87) PCT Pub. No.: WO03/085017

PCT Pub. Date: Oct. 16, 2003

(65) Prior Publication Data

US 2005/0148755 A1 Jul. 7, 2005

(30) Foreign Application Priority Data

Apr. 11, 2002 (DE) ................ 102 15 973

(51) Int. Cl.
*C08G 2/08* (2006.01)
*C08G 2/06* (2006.01)

(52) U.S. Cl. ............ 528/236; 528/230; 528/425; 528/403; 528/485; 528/486

(58) Field of Classification Search ........ 528/425, 528/403, 485, 486, 236, 230
See application file for complete search history.

(56) References Cited

U.S. PATENT DOCUMENTS 3,457,227 A 7/1969 Kennedy

FOREIGN PATENT DOCUMENTS

GB 1187233 4/1970
WO 94/09055 4/1994

OTHER PUBLICATIONS

F. Edelmann et al., "Übergangsmetall-Fulven-Komplexe", *Journal of Organometallic Chemistry*, vol. 309, 1986, pp. 87-108.
Chaloyard et al., "Synthesis of Ring-Substituted Derivatives of Cyclopentadienyl Tricarbonyl Complexes of Molybdenum and Tungsten", *Inorganic Chemistry*, vol. 19, 1980, 3217-3220.

*Primary Examiner*—Duc Truong
(74) *Attorney, Agent, or Firm*—Novak Druce & Quigg, LLP

(57) ABSTRACT

A process is described for preparing polyoxymethylene by contacting a formaldehyde source with a catalyst of the formula I $$[Cp_vML_w]^{m+}Z_{m/n}^{n-} \qquad (I)$$

where
M is Ti, Zr, Hf, V, Nb, Ta, Cr, Mo, W, Mn, Re, Fe, Ru, Os, Co, Rh or Ir,
Cp is a cyclopentadienyl ligand $C_5H_{(5-u)}R^1_u$, where
u is from 0 to 5 and
$R^1$ is alkyl, alkenyl, aryl, heteroaryl, aralkyl, $COOR^2$, $COR^2$, CN or $NO_2$, and
$R^2$ is H, alkyl, aryl or aralkyl,
v is 1 or 2,
each L is independently a nitrile, CO or a ligand displaceable by CO,
w is an integer from 0 to 4,
Z is an anion, and
m and n are each independently an integer from 1 to 3.

9 Claims, No Drawings

PRODUCTION OF POLYOXYMETHYLENE AND SUITABLE (II) CATALYSTS

The present invention relates to a process for preparing polyoxymethylene by contacting a formaldehyde source with a catalyst and a catalyst suitable therefor.

The polyoxymethylene resulting from the homopolymerization of formaldehyde is a polymer having repeating $CH_2O$ units. When formaldehyde is copolymerized with cyclic ethers or formals, the $CH_2O$ chains are interrupted by units which stem from the cyclic ethers or formals. The term polyoxymethylene is used hereinbelow both for the homo- and for the copolymer.

Polyoxymethylene and processes for preparing it by homo- or copolymerizing formaldehyde using metal complexes as catalysts are well known. For instance, WO 94/09055 describes the polymerization of cyclic ethers, such as epoxides, THF and trioxane, in the presence of a catalyst of the general formula $MZ_sQ_t$, where M is a metal, at least one Z is a perfluorinated alkylsulfonate and any further Z moieties present are each oxo or a monovalent monoanion, Q is a neutral ligand, s is from 2 to 5 and t is from 0 to 6. The polymerization is carried out in the further presence of a carboxylic anhydride, an acyl chloride or a carboxylic acid having a $pK_a$ in water of less than 2 as an accelerant. Specifically, the polymerization of trioxane in the presence of ytterbium triflate is described. However, the unsatisfactory yields even at long reaction times are disadvantageous.

The prior art processes have long induction times, in particular when the formaldehyde source is not highly pure. This may even lead to no polymerization occurring at all. The induction time is the time which elapses from the mixing of the formaldehyde source with the catalyst to the "light-off" of the polymerization. A long induction time leads to long residence times of reactants in the reactor which is uneconomical.

It is an object of the present invention to provide a process having a short induction time which is preferably tolerant toward impurities and water traces in the formaldehyde source.

We have found that this object is achieved by a process for preparing polyoxymethylene by contacting a formaldehyde source with a catalyst of the formula I $$[Cp_vML_w]^{m+}Z_{m/n}^{n-} \qquad (I)$$

where

M is Ti, Zr, Hf, V, Nb, Ta, Cr, Mo, W, Mn, Re, Fe, Ru, Os, Co, Rh or Ir,

Cp is a cyclopentadienyl ligand $C_5H_{(5-u)}R^1_u$, where u is from 0 to 5 and each R$^1$ is independently alkyl, alkenyl, aryl, heteroaryl, aralkyl, COOR$^2$, COR$^2$, CN or NO$_2$, and R$^2$ is H, alkyl, aryl or aralkyl, v is 1 or 2, each L is independently a nitrile, Co or a ligand displaceable by CO, w is an integer from 0 to 4, Z is an anion, and m and n are each independently an integer from 1 to 3.

Preference is given to not using any carboxylic anhydrides, acyl chlorides or carboxylic acids having a $pK_a$ in water of less than 2 as accelerants.

For the purposes of the present invention, the term "alkyl" encompasses linear, branched and cyclic alkyl groups. These are preferably $C_1$–$C_{20}$-alkyl, in particular $C_1$–$C_6$-alkyl groups, such as methyl, ethyl, propyl, isopropyl, n-butyl, 2-butyl, isobutyl, tert-butyl, n-pentyl and n-hexyl, or $C_3$–$C_8$-cycloalkyl, such as cyclopropyl, cyclopentyl, cyclohexyl or cycloheptyl.

The halogenated radicals are preferably chlorinated and/or fluorinated, more preferably fluorinated, in particular perfluorinated radicals, in particular alkyl radicals.

Aryl is preferably $C_6$–$C_{14}$-aryl, such as phenyl, naphthyl, anthracenyl or phenanthrenyl and in particular phenyl or naphthyl. The aryl radicals may carry up to three $C_1$–$C_4$-alkyl radicals.

Aralkyl is preferably $C_7$–$C_{20}$-aralkyl, such as benzyl or phenylethyl.

The term "alkenyl" encompasses linear, branched and cyclic alkenyl groups. These are preferably $C_2$–$C_{20}$-alkenyl groups, in particular $C_2$–$C_6$-alkenyl groups, such as ethenyl, propenyl, isopropenyl, n-butenyl, isobutenyl, n-pentenyl and n-hexenyl, or $C_5$–$C_8$-cycloalkenyl, such as cyclopentenyl, cyclohexenyl, cycloheptenyl or cyclooctenyl.

In formula I, M is preferably Mo or W.

Cp is preferably a cyclopentadienyl ligand $C_5H_{(5-u)}R^1_u$, 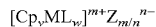 where R$^1$ is methyl, CHO, COCH$_3$, COC$_2$H$_5$, COOCH$_3$, COOC$_2$H$_5$, CN or NO$_2$. Particular preference is given to those cyclopentadienyl ligands Cp where R$^1$ is CHO, COCH$_3$, COC$_2$H$_5$, COOCH$_3$ or COOC$_2$H$_5$ and u is 1 or 2. In particular, when u is 1, R$^1$ is CHO, COCH$_3$, COC$_2$H$_5$ or COOCH$_3$; when u is 2, R$^1$ is in particular COOC$_2$H$_5$, and the two R$^1$ radicals may be neighboring or nonneighboring. R$^1$ may be methyl when u is 5.

The ligands L are a nitrile, CO or another ligand which, owing to the high affinity of CO toward the central atom, for example Mo, can be displaced by CO from the coordination sphere of a complex. The ease with which a ligand is displaced by another generally correlates with its position in the spectrochemical series of ligands so that, as well as CO, suitable ligands L include those ligands which lead to a smaller ligand field splitting than CO. A ligand is considered to be displaceable by CO when it can be displaced thermally or photochemically by CO from a complex in solid or dissolved form (in toluene or $CH_2Cl_2$) at a pressure of less than 100 bar of CO.

Preference is given to selecting L from nitriles, CO, alkenes, amines displaceable by CO, ethers displaceable by CO, carboxylic esters, cyclic carbonic esters, epoxides, hemiacetals, acetals and nitro compounds.

The term "nitrile" encompasses in particular compounds of the general formula R$^3$CN, where R$^3$ is an optionally halogenated alkyl, aryl or aralkyl radical. R$^3$ is more preferably methyl, ethyl, propyl, isopropyl, n-butyl, isobutyl, sec-butyl or tert-butyl.

Examples of useful nitriles include acetonitrile, propionitrile and benzonitrile.

Amines displaceable by CO are in particular aromatic amines and amines having a sterically shielded nitrogen atom. Examples of useful amines include diisopropylamine, N,N-dimethylaniline and diphenylamine.

Ethers displaceable by CO are in particular both open-chain ethers having electron-withdrawing and/or sterically demanding radicals and also cyclic ethers. The preferred open-chain ethers include diphenyl ether and methyl tert-butyl ether. Preferred cyclic ethers are tetrahydrofuran and 1,4-dioxane.

Carboxylic esters encompass in particular compounds of the general formula R$^4$COOR$^5$, where R$^4$ and R$^5$ are each independently as defined for R$^3$. R$^4$ may also be H. R$^4$ and R$^5$ may also form a bridging unit. R$^4$ and R$^5$ are preferably each independently methyl, ethyl, propyl, isopropyl, n-butyl or phenyl. Examples of useful carboxylic esters include methyl acetate and ethyl acetate.

Cyclic carbonic esters encompass in particular compounds of the general formula $R^6OCOOR^7$ where $R^6$ and $R^7$ together form a $C_2$–$C_4$-alkylene bridge which may be partly or fully halogenated or carry from 1 to 4 alkyl radicals. Examples of useful cyclic carbonic esters include ethylene carbonate and propylene carbonate.

Epoxides encompass in particular compounds of the general formula

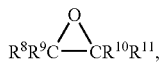

where $R^8$, $R^9$, $R^{10}$ and $R^{11}$ are each independently as defined for $R^3$ or are H.

Examples of useful epoxides include ethylene oxide, propylene oxide and butylene oxide.

Hemiacetals and acetals encompass in particular compounds of the general formula $R^{12}OCR^{13}R^{14}OH$ and $R^{12}OCR^{13}R^{14}OR^{15}$, where $R^{12}$, $R^{13}$, $R^{14}$ and $R^{15}$ are each independently as defined for $R^3$, and $R^{13}$ and $R^{14}$ may also be H or together form a $C_3$–$C_7$-alkylene bridge, and $R^{12}$ and $R^{15}$ may also form a $C_2$–$C_4$-alkylene bridge which may be interrupted by one or two oxygen atoms. Examples of useful acetals include trioxane, 1,3-dioxane, 1,3-dioxepane and cyclopentanone dimethylacetal.

Nitro compounds encompass in particular compounds of the general formula $R^{16}NO_2$, were $R^{16}$ is as defined for $R^3$. Examples of useful nitro compounds include nitromethane and nitrobenzene.

Particular preference is given to selecting the ligands L from acetonitrile and CO and they are in particular CO.

w is preferably from 1 to 4.

z is an anion, preferably an anion derived from a Brönsted acid whose $pK_a$ is smaller than that of acetic acid or a noncoordinating anion. The term "noncoordinating anion" is known to those skilled in the art. These are anions where the charge is effectively distributed over more than one atom so that there are no point-centered charges. Z is more preferably a halide, a sulfonate of the general formula $ROSO_2$—, where R is alkyl, partly or fully halogenated alkyl or aryl, such as trifluoromethanesulfonate, benzenesulfonate or p-toluenesulfonate, a carboxylate of the general formula R'COO—, where R' is as defined for R and more preferably fully halogenated alkyl, in particular perfluorinated alkyl, such as trifluoroacetate, a complexed borate such as tetrafluoroborate or tetraphenylborate, a complexed phosphate such as hexafluorophosphate, a complexed arsenate such as hexafluoroarsenate or a complexed antimonate such as hexafluoro- or hexachloroantimonate. Z is in particular chloride, trifluoromethanesulfonate or trifluoroacetate.

The catalyst I is preferably used in a quantity of from 1 ppm to 1 mol %, more preferably from 5 to 1000 ppm and in particular from 50 to 500 ppm, based on the formaldehyde source.

Preference is given to preparing the catalyst I before use in the polymerization. The catalyst is prepared by customary processes for preparing cyclopentadienyl metal complexes. For example, an alkali metal salt of the corresponding cyclopentadienide, for example the sodium or lithium salt, is reacted with a carbonyl complex of the metal M and then with an alkylating agent, for example methyl iodide. The resulting complex is then reacted with the corresponding Bronsted acid of Z or with a salt of Z to give the catalyst I.

The formaldehyde source used is preferably formaldehyde, trioxane, tetraoxane or paraformaldehyde or a mixture thereof, and more preferably formaldehyde or trioxane or a mixture thereof. Trioxane, the cyclic trimer of formaldehyde, and paraformaldehyde, an oligomer having from 2 to 100 formaldehyde units, are either depolymerized before use in the polymerization reaction or preferably used as such and dissociated in the course of the reaction.

The formaldehyde source preferably has a degree of purity of at least 95%, more preferably at least 98% and in particular at least 99%. In particular, the formaldehyde source contains a maximum of 0.002% by weight of compounds having active hydrogen such as water, methanol or formic acid, based on the weight of the formaldehyde source. However, the process according to the invention also tolerates formaldehyde sources having a lower degree of purity and a higher content of compounds having active hydrogen.

The process according to the invention may be carried out as a solution, suspension, gas phase or bulk polymerization.

When the polymerization is carried out in solution or suspension, it is advantageous to select a substantially anhydrous aprotic organic reaction medium which is liquid under the reaction conditions and reacts neither with the catalyst nor with the formaldehyde source. When the polymerization is carried out in solution, the solvent should advantageously also dissolve the catalyst and the formaldehyde source but preferably not dissolve or only sparingly dissolve the polyoxymethylene formed. When the polymerization is carried out in suspension, the formaldehyde source should also be insoluble in the solvent and, if necessary, dispersion auxiliaries are used, in order to achieve better distribution of the formaldehyde source in the reaction medium. Preference is given to selecting the solvent from saturated or unsaturated, linear or branched, aliphatic hydrocarbons which may be partly or fully halogenated, optionally substituted alicycles, optionally substituted fused alicycles, optionally substituted aromatics, acyclic and cyclic ethers, polyether polyols and other polar aprotic solvents such as sulfoxides and carboxylic acid derivatives.

Examples of useful aliphatic hydrocarbons include propane, n-butane, n-pentane, n-hexane, n-heptane, n-decane and mixtures thereof. Examples of useful halogenated hydrocarbons include methylene chloride, chloroform, carbon tetrachloride, dichloroethane or trichloroethane. Useful aromatics include benzene, toluene, the xylenes, nitrobenzene, chlorobenzene, dichlorobenzene and biphenyl. Useful alicycles include cyclopentane, cyclohexane, tetralin and decahydronaphthalene. Examples of useful acyclic ethers include diethyl ether, dipropyl ether, diisopropyl ether, dibutyl ether and butyl methyl ether; useful cyclic ethers include tetrahydrofuran and dioxane. Examples of the useful polyether polyols include dimethoxyethane and diethylene glycol. An example of a useful sulfoxide is dimethyl sulfoxide. The useful carboxylic acid derivatives include dimethylformamide, ethyl acetate, acetonitrile, acrylates and ethylene carbonate.

Particularly preferred solvents for the solution polymerization are selected from the following: n-hexane, cyclohexane, methylene chloride, chloroform, dichloroethane, trichloroethane, tetrachloroethane, benzene, toluene, nitrobenzene, chlorobenzene, dichlorobenzene, tetrahydrofuran and acetonitrile. All mixtures thereof are also suitable.

Preference is given to using the formaldehyde source in the solution polymerization in a concentration of from 20 to 90% by weight, preferably from 30 to 80% by weight, based on the total weight of the solution. The polymerization in solution may also be carried out as a "blow-in" polymerization. This involves continuously blowing the formaldehyde source, in particular formaldehyde gas, into a solution which contains the catalyst.

Preferred reaction media for the heterogeneous suspension polymerization include straight-chain aliphatic hydrocarbons.

The polymerization may also be carried out in bulk when trioxane is used as the formaldehyde source. Trioxane is used as a melt; the reaction temperature and reaction pressure are selected correspondingly.

In the process according to the invention, the sequence in which the formaldehyde source and the catalyst I are introduced into the reaction zone is not of decisive importance. However, preference is given to initially charging the formaldehyde source and adding the catalyst to it.

The polymerization is preferably carried out at a temperature of from −40 to 150° C., more preferably from 0 to 150° C. The solution polymerization and suspension polymerization are carried out in particular at from 20 to 100° C. and especially from 30 to 90° C. The bulk polymerization is preferably carried out at such a temperature that the formaldehyde source, especially trioxane, and the polymer are in the form of a melt. In particular, the temperature, depending on the pressure, is from 60 to 120° C., especially from 60 to 100° C.

The reaction pressure is preferably from 0.1 to 50 bar, more preferably from 0.5 to 10 bar and in particular from 1 to 5 bar.

Useful reaction apparatus includes the reactors which are known to the skilled in the art for the type and conditions of each different polymerization.

The above remarks apply both to the homopolymerization of the formaldehyde source and to the copolymerization of the formaldehyde source with cyclic ethers or formals which will be referred to hereinbelow as comonomers.

Homopolymeric polyoxymethylene tends to thermally degrade, i.e. to depolymerize to oligomeric or monomeric formaldehyde. This is attributed to the presence of hemiacetal functions at the chain ends of the polyoxymethylene. Copolymerization of formaldehyde with comonomers such as cyclic ethers and/or formals can stabilize the polyoxymethylene formed. These comonomers are incorporated in the polyoxymethylene chain. When the polymer is subjected to thermal stress, the polyoxymethylene chain degrades until the chain end is formed by one of the above-mentioned comonomers. These are substantially less prone to thermally degrade, so that the depolymerization comes to a stop and the polymer is stabilized. Useful comonomers of this type are cyclic ethers, in particular those of the formula

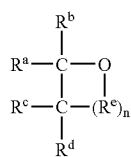

where $R^a$, $R^b$, $R^c$ and $R^d$ are each independently hydrogen or an optionally halogenated $C_1$–$C_4$-alkyl group, $R^e$ is a —$CH_2$—, —$CH_2O$—, a $C_1$–$C_4$-alkyl- or $C_1$–$C_4$-haloalkyl-substituted methylene group or a corresponding oxymethylene group and n is an integer from 0 to 3.

Cyclic ethers mentioned only by way of example include ethylene oxide, 1,2-propylene oxide, 1,2-butylene oxide, 1,3-butylene oxide, 1,3-dioxane, 1,3-dioxolane and 1,3-dioxepane, and comonomers mentioned only by way of example include linear oligo- and polyformals such as polydioxolane and polydioxepane.

When they are used, repeat units of the formula

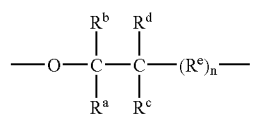

are incorporated into the polyoxymethylene copolymers obtained in addition to the —$CH_2O$— repeat units stemming from the formaldehyde source.

If desired, a third monomer may be used in addition to the above-described cyclic ethers, preferably a bifunctional compound of the formula

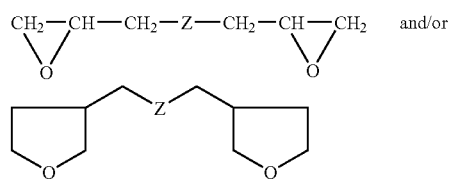

where Z is a chemical bond, —O—, —ORO— (R=$C_1$–$C_8$-alkylene or $C_2$–$C_8$-cycloalkylene).

To name only a few examples, preferred monomers of this type include ethylene diglycide, diglycidyl ethers and diethers made from glycidylene and formaldehyde, dioxane or trioxane in a molar ratio of 2:1 and also diethers made from 2 mol of glycidyl compound and 1 mol of an aliphatic diol having from 2 to 8 carbon atoms, for example the diglycidyl ethers of ethylene glycol, 1,4-butanediol, 1,3-butanediol, cyclobutane-1,3-diol, 1,2-propanediol and cyclohexane-1,4-diol.

Particular preference is given to using ethylene oxide, 1,2-propylene oxide, tetrahydrofuran, 1,3-dioxane, 1,4-dioxane, 1,3-dioxolane and 1,3-dioxepane, in particular 1,3-dioxepane as comonomers.

The comonomers are preferably used in a quantity of from 0.1 to 40% by weight, more preferably from 0.2 to 10% by weight, in particular from 0.5 to 5% by weight, based on the formaldehyde contained in the formaldehyde source.

The comonomers may either be initially charged with the formaldehyde source or added to the initially charged catalyst together with the formaldehyde source. Alternatively, they may be added to the reaction mixture consisting of the formaldehyde source and the catalyst.

When cyclic ethers are used as comonomers, there is a risk that these contain peroxides, in particular when they have been stored for a relatively long time before use. Peroxides firstly lengthen the induction time of the polymerization and secondly reduce the thermal stability of the polyoxymethylene formed owing to their oxidative effect.

For this reason, preference is given to using cyclic ethers which contain less than 0.0015% by weight, more preferably less than 0.0005% by weight, of peroxides, reported as hydrogen peroxide and based on the quantity of cyclic ether used.

In order to prevent oxidative degradation of the polyoxymethylenes obtained, preference is given to adding sterically hindered phenol antioxidants to them. In principle, useful sterically hindered phenols include all compounds having a phenolic structure which have at least one sterically demanding group on the phenolic ring.

Preference is given to using, for example, compounds of the formula

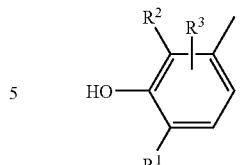

where $R^1$ and $R^2$ are identical or different and are each an alkyl group, a substituted alkyl group or a substituted triazole group and $R^3$ is an alkyl group, a substituted alkyl group, an alkoxy group or a substituted amino group.

Antioxidants of the type mentioned are described, for example, in DE-A 27 02 661 (U.S. Pat. No. 4,360,617).

A further group of preferred sterically hindered phenols is derived from substituted benzenecarboxylic acids, in particular from substituted benzenepropionic acids.

Particularly preferred compounds from this class are compounds of the formula

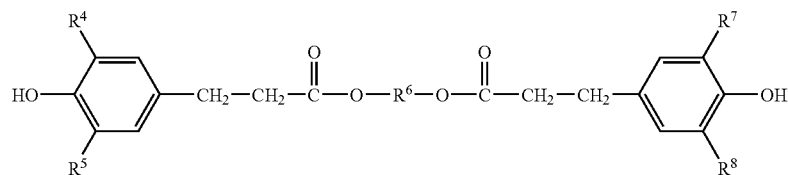

where $R^4$, $R^5$, $R^7$ and $R^8$ are each independently $C_1$–$C_8$-alkyl groups which may themselves be substituted (at least one of them is a sterically demanding group) and $R^6$ is a bivalent aliphatic radical having from 1 to 10 carbon atoms which may also have C—O-bonds in the main chain.

Preferred compounds of this type are

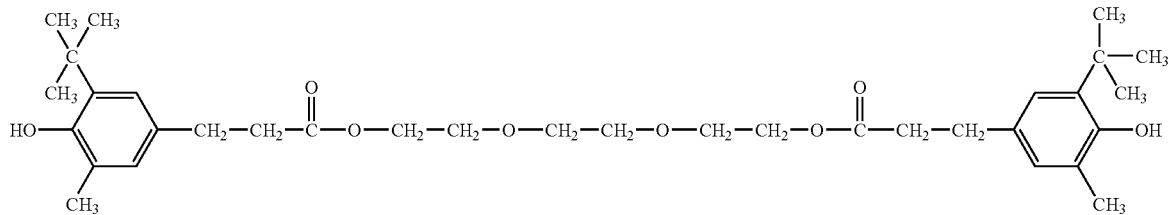

(Irganox® 245 from Ciba-Geigy)

and

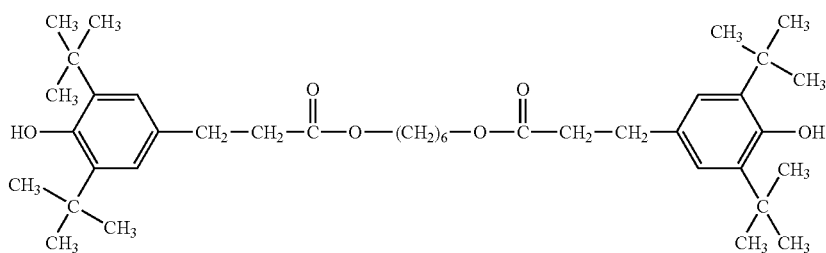

(Irganox® 259 from Ciba-Geigy)

Examples of sterically hindered phenols include:
2,2'-methylene-bis(4-methyl-6-tert-butylphenol), 1,6-hexanediolbis[3-(3,5-di-tert-butyl-4-hydroxyphenyl)-propionate] (Irganox® 259), pentaerythrityl tetrakis[3-(3,5-di-tert-butyl-4-hydroxyphenyl)propionate] and the above-described Irganox® 245

The following compounds have proven to be particularly effective and are therefore used with preference:
2,2'-methylene-bis(4-methyl-6-tert-butylphenol), 1,6-hexanediolbis[3-(3,5-di-tert-butyl-4-hydroxyphenyl)-propionate] (Irganox® 259), pentaerythrityl tetrakis[3-(3,5-di-tert-butyl-4-hydroxyphenyl)propionate], distearyl 3,5-di-tert-butyl-4-hydroxybenzylphosphonate, 2,6,7-trioxa-1-phosphabicyclo[2.2.2]oct-4-yl-methyl 3,5-di-tert-butyl-4-hydroxycinnamate, 3,5-di-tert-butyl-4-hydroxyphenyl-3,5-distearyl-thiotriazylamine, 2-(2'-hydroxy-3'-hydroxy-3',5'-di-tert-butylphenyl)-5-chloro-benzotriazole, 2,6-di-tert-butyl-4-hydroxymethylphenol, 1,3,5-trimethyl-2,4,6-tris-(3,5-di-tert-butyl-4-hydroxybenzyl) benzene, 4,4'-methylene-bis(2,6-di-tert-butylphenol), 3,5-di-tert-butyl-4-hydroxybenzyldimethylamine and N,N'-hexamethylene-bis-3,5-di-tert-butyl-4-hydroxyhydrocinnamide.

The sterically hindered phenols which may be used individually or as a mixture may either be added to the monomer mixture or to the finished polymer. In the latter case, the polymer may optionally be melted in order to achieve better dispersion of the antioxidant.

Preference is given to using the antioxidants in a quantity of up to 2% by weight, more preferably from 0.001 to 2% by weight, in particular from 0.005 to 1% by weight, based on the weight of monomer mixture used or polymer obtained.

Another possible way of stabilizing the polyoxymethylene obtained by homopolymerization of a formaldehyde source is to cap the hemiacetal end groups. i.e. convert them to functionalities which do not tend to thermally degrade. To this end, the polyoxymethylene is reacted, for example, with carboxylic acids, acyl halides, carboxylic anhydrides, carbonates or hemiacetals, or cyanethylated.

In this variant, the polyoxymethylene is stabilized in a separate step following the polymerization. Preference is accordingly given to stabilizing the polyoxymethylene by copolymerization with the comonomers which requires no separate step.

After the end of the polymerization reaction, preference is given to admixing the catalyst with a deactivator. Useful deactivators include ammonia, aliphatic and aromatic amines, alcohols, basic salts such as alkaline metal and alkaline earth metal hydroxides and carbonates or borax, and also water. The deactivated catalyst and the deactivator are then separated from the polymer, preferably by washing with water or an organic solvent such as acetone or methylene chloride. However, since the catalyst I may also be used in very small quantities, subsequent treatment of the polyoxymethylene to remove the catalyst may optionally also be omitted.

After the end of the polymerization reaction, excess monomer which is still present in the reaction zone may be removed, for example, by distillation, by purging with a gas stream, for example air or nitrogen, by degassing, by solvent extraction or by washing with an aqueous mixture or with an organic solvent such as acetone.

The polyoxymethylene is generally recovered by removing the solvent or, in the case of bulk polymerization, by cooling and optionally granulating the melt. A preferred workup for bulk polymerization comprises the discharge, cooling and granulating of the polymer melt at elevated pressure and in the presence of a liquid, in particular of water, and is described in German patent application DE-A-100 06 037 which is fully incorporated herein by way of reference.

In the process according to the invention, induction times are obtained which are in the optimal range for industrial applications of from a few seconds to a few minutes. At the same time, the catalyst quantity required is small. The polyoxymethylene preparable according to the invention has number average molar masses of well above 10,000 g/mol. The number average molar mass Mn is preferably at least 9000 g/mol, more preferably at least 10,000 g/mol. The weight average molar mass Mw is preferably at least 20,000 g/mol, more preferably at least 30,000 g/mol. The polydispersity index PDI ($M_w/M_n$) is preferably less than 4, more preferably less than 3.

The invention further provides a catalyst of the formula Ia $$[CpM(CO)_2)L]^+Z_{1/n}{}^{n-} \quad \text{(Ia)}$$

where
M is Mo or W,
Cp is a cyclopentadienyl ligand $C_5H_4R^1$ or $C_5H_3R^1{}_2$, where $R^1$ is CHO, $COCH_3$, $COOCH_3$ or $COOC_2H_5$,
L is CO or $CH_3CN$,
Z is an anion and
n is an integer from 1 to 3.

In the cyclopentadienyl ligand $C_5H_4R^1$, $R^1$ is preferably CHO, $COCH_3$ or $COOCH_3$, and in the cyclopentadienyl ligand $C_5H_3R^1{}_2$ is preferably $COOC_2H_5$, and in the latter case, the individual $R^1$ radicals may be neighboring or nonneighboring.

Z is preferably trifluoromethanesulfonate, trifluoroacetate, tetrafluoroborate, hexafluorophosphate or hexafluoroantimonate and in particular trifluoromethanesulfonate.

The remarks made relating to the process according to the invention are applied correspondingly to the catalyst according to the invention.

The invention is illustrated by the examples hereinbelow.

EXAMPLES

1. Preparation of the Catalysts

The catalysts were prepared under protective gas. The following catalysts were synthesized:

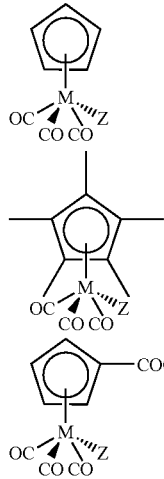

I.1: M = Mo; Z = CF$_3$SO$_3$
I.2: M = W; Z = CF$_3$SO$_3$
I.5: M = Mo; Z = BF$_4$
I.6: M = Mo; Z = CF$_3$COO

I.3: M = Mo; Z = CF$_3$SO$_3$
I.4: M = W; Z = CF$_3$SO$_3$

I.7: M = Mo; Z = CF$_3$SO$_3$
I.8: M = W; Z = CF$_3$SO$_3$

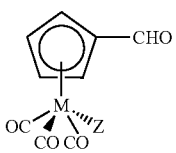 I.9: M = Mo; Z = CF$_3$SO$_3$

1.1 Synthesis of I.1 and I.2

The catalysts of the formulae I.1 and I.2 were prepared by the process described by M. Appel et al. in J. Organomet. Chem. 1987, 322, 77.

1.2 Synthesis of I.3 and I.4

The catalysts I.3 and I.4 were likewise prepared by the process described by M. Appel et al. in J. Organomet. Chem. 1987, 322, 77.

1.3 Synthesis of I.5

The catalyst I.5 was also synthesized by the process described by M. Appel et al. in J. Organomet. Chem. 1987, 322, 77.

1.4 Synthesis of I.6

The catalyst I.6 was prepared by the process described by R. B. King et al. in J. Organomet. Chem. 1968, 15, 457.

1.5 Synthesis of I.7

5.901 g (33.5 mmol) of the 1,4-dioxane complex of cyclopentadienylsodium were heated with 9.008 g (100.0 mmol) of dimethyl carbonate in 70 ml of tetrahydrofuran to reflux. After 3 h, the solvent and excess dimethyl carbonate were removed distillatively and the residue was washed with 150 ml of diethyl ether. After drying under reduced pressure, 4.68 g (32.03 mmol) of methylcarboxycyclopentadienylsodium were obtained. 2.913 g (19.94 mmol) of methylcarboxycyclopentadienylsodium were admixed with 4.854 g (18.39 mmol) of Mo(CO)$_6$ in 80 ml of tetrahydrofuran, heated for 24 h to reflux, admixed with 4.55 g (32.06 mmol) of methyl iodide after cooling to room temperature and stirred for a further 24 hours at room temperature. After distillative removal of the solvent and the excess methyl iodide under reduced pressure, the crude product was subjected to purification by column chromatography (activated silica gel; cyclohexane:dichloromethane=5:2) to obtain 3.853 g (12.11 mmol) of ($\eta^5$-methylcarboxycyclopentadienyl)triscarbonylmethylmolybdenum (II) as a yellow powder. 0.4598 g (1.445 mmol) of ($\eta^5$-methylcarboxycyclopentadienyl)triscarbonylmethylmolybdenum (II) in 20 ml of dichloromethane was gradually admixed at −20° C. with a solution of 0.2169 g (1.4453 mmol) of trifluoromethanesulfonic acid in 5 ml of dichloromethane which caused the yellow solution to turn wine red and vigorous gas formation to occur. The reaction temperature was gradually increased to room temperature in 5° steps at 30 minute intervals. The reaction mixture was then admixed with 25 ml of n-hexane and concentrated under reduced pressure until a wine red product precipitated. The remaining solvent was pipetted off and the solid dried under reduced pressure. 0.443 g (0.9797 mmol, 68% of theory) of ($\eta^5$-methylcarboxycyclopentadienyl)triscarbonylmolybdenum(II) triflate (I.7) was obtained as a wine red powder.

Spectroscopic Data:

$^1$H-NMR (CDCl$_3$): 6.12 (m); 5.92 (m); 3.76 (s, OCH$_3$)

$^{13}$C-NMR (CDCl$_3$): 237.0; 223.4 (CO); 163.7 (ester); 100.1; 97.6 (Cp); 53.0 (OCH$_3$)

MS (FD): 451 (M$^+$, 20%); 426 (M$^+$—CO)

IR (KBr disk): 3115; 2961; 2075; 1986; 1732; 1290; 1234; 1201; 1008

| Elemental analysis: | Found | Calculated |
|---|---|---|
| C | 28.97 | 29.22 |
| H | 1.69 | 1.56 |
| S | 7.57 | 7.09 |

1.6 Synthesis of I.8

2.486 g (17.01 mmol) of methylcarboxycyclopentadienylsodium which was prepared as described in 1.5 was admixed with 6.675 g (13.70 mmol) of W(CO)$_3$(dmf)$_3$ in 80 ml of DMF, heated for 3 h to reflux and then the solvent was evaporated to dryness. The remaining brown oil was taken up in 80 ml of THF and admixed with 4.55 g (32.06 mmol) of methyl iodide. After stirring for 24 hours at room temperature, the workup was effected as described in I.5. 3.97 g (9.78 mmol; 71% of theory) of ($\eta^5$-methylcarboxycyclopentadienyl)triscarbonylmethyltungsten (II) were obtained as a yellow powder. 0.763 g (1.879 mmol) of ($\eta^5$-methylcarboxycyclopentadienyl)triscarbonylmethyltungsten (II) in 20 ml of dichloromethane was gradually admixed at room temperature with a solution of 0.2679 g (1.785 mmol) of trifluoromethanesulfonic acid in 10 ml of dichloromethane which caused the yellow solution to turn wine red and vigorous gas development to occur. After stirring for 1 h at room temperature, the solvent was removed completely under reduced pressure. The brick red residue was dissolved in 10 ml of dichloromethane and admixed with 10 ml of n-hexane. The mixture was concentrated under reduced pressure until the red product precipitated. The remaining solvent was pipetted off by hand and the remaining solid dried under reduced pressure. 0.710 g (1.315 mmol, 70% of theory) of ($\eta^5$-methylcarboxycyclopentadienyl)triscarbonyltungsten (II)triflate (I.8) was obtained as a wine red powder.

Spectroscopic Data:

$^1$H-NMR (CDCl$_3$): 6.28 (m); 6.12 (m); 3.84 (s, OCH$_3$)

$^{13}$C-NMR (CDCl$_3$): 226.1; 217.1 (CO); 163.7 (ester); 99.3; 95.6; 94.6; 53.1 (OCH$_3$)

MS (FD): 540 (M+, 100%); 512 (M$^+$-CO)

IR (KBr disk): 3115; 2962; 2064; 1989; 1961; 1731; 1294; 1234; 1189; 1005

| Elemental analysis: | Found | Calculated |
|---|---|---|
| C | 24.12 | 24.46 |
| H | 1.15 | 1.31 |
| S | 6.39 | 5.94 |

1.7 Synthesis of I.9

5.231 g (26.89 mmol) of the 1,4-dioxane complex of cyclopentadienylsodium were heated to reflux with 6.014 g (100.15 mmol) of methyl formate in 60 ml of tetrahydrofuran. After 3 h, the solvent and excess methyl formate were removed distillatively and the residue washed with 150 ml of diethyl ether. After drying under reduced pressure, 2.70 g (23.26 mmol; 78% of theory) of formylcyclopentadienylsodium were obtained. 0.993 g (8.55 mmol) of formylcyclopentadienylsodium was admixed with 2.564 g (8.46 mmol) of Mo(CO)$_3$(CH$_3$CN)$_3$ in 100 ml of THF, heated to reflux for 2 h and then admixed at room temperature with 2.147 g (8.46 mmol) of iodine. After distillative removal of the solvent, the crude product was subjected to purification by column chromatography (activated silica gel; dichloromethane) and 1.078 g (3.03 mmol; 36% of theory) of ($\eta^5$-formylcyclopentadienyl)triscarbonyliodomolybdenum (II) were obtained as a red-brown powder. 0.2822 g (0.793 mmol) of ($\eta^5$-formylcyclopentadienyl)triscarbonyliodomolybdenum (II) in 20 ml of acetonitrile was admixed at room temperature with a solution of 0.2037 g (0.793 mmol) of silver trifluoromethanesulfonate in 5 ml of acetonitrile and heated to reflux for 4 h which caused an ochre suspension to form from the clear red-brown solution. This was filtered through a frit (porosity 3) reinforced by 2 cm of activated silica gel. The red filtrate was concentrated to dryness, taken up in 20 ml of dichloromethane and admixed with the same quantity of n-hexane. The mixture was concentrated under reduced pressure to 8 ml, the remaining solvent was pipetted off by hand and the solid dried under reduced pressure. 0.224 g (0.515 mmol, 65% of theory) of ($\eta^5$-formylcyclopentadienyl)biscarbonyl(acetonitrilo)molybdenum (II)triflate (I.9) was obtained as a light red powder.

Spectroscopic Data:

$^1$H-NMR (CDCl$_3$): 9.68 (s); 6.11 (m); 5.98 (m); 2.54 (s, CH$_3$CN)

$^{13}$C-NMR (CDCl$_3$): 244.4 (CO); 187.3 (Formyl); 143.2 (CN); 103.3; 94.6 (Cp); 5.4 (CH$_3$CN)

MS (FD): 288 (M$^+$—OTf)

IR (KBr disk): 3091; 3006; 2948; 2313; 1994; 1911; 1688; 1264; 1226; 1168; 1149; 1030

| Elemental analysis: | Found | Calculated |
|---|---|---|
| C | 29.88 | 30.36 |
| H | 2.05 | 1.85 |
| N | 4.35 | 3.22 |
| S | 7.28 | 7.37 |

2. Polymerization

The polymerizations were effected without protective gas.

2.1 Bulk Polymerization 250 ml round-bottom flasks were charged with 6 ml of trioxane and 200 µl of 1,3-dioxepane and each admixed with a solution of the catalysts listed in Table 1 in the appropriate quantity in 1 ml of dichloromethane at 80° C. The time between addition of the catalyst and the onset of cloudiness was measured as the induction time. After 2 h, the reaction mixture was cooled and the solvent removed. The crude polymer was comminuted using a mortar and admixed with 50 ml of an aqueous 0.2 M sodium carbonate solution. This mixture was heated for 16 h to reflux. The reaction mixture was then filtered and the filter cake washed with 25 ml of water and 25 ml of acetone. The filter cake was dried at 70° C. for 16 h. In the following table, the induction times measured and also the number average and the weight average molar masses $M_n$ and $M_w$ of the polyoxymethylene obtained, the polydispersity index (PDI=$M_w/M_n$) and the crude yields are reported. The molar masses $M_n$ and $M_w$ were determined by means of gel permeation chromatography.

TABLE 1

| Catalyst | Quantity [mmol] | Induction time [s] | $M_w$ [kg/mol] | $M_n$ [kg/mol] | PDI | Crude yield [g] |
|---|---|---|---|---|---|---|
| I.1 | 0.0254 | 60 | 32.4 | 12.9 | 2.51 | 6.34 |
| I.2 | 0.0208 | 80 | 112 | — | — | 6.45 |
| I.3 | 0.0289 | 120 | 20.7 | 9.20 | 2.25 | 6.20 |
| I.4 | 0.0232 | 300 | 23.2 | 10.3 | 2.25 | 7.16 |
| I.7 | 0.0086 | 15 | 22.4 | 9.20 | 2.43 | 6.61 |
| I.8 | 0.0100 | 15 | 31.3 | 12.5 | 2.50 | 6.14 |
| I.9 | 0.0284 | 30 | 35.0 | 10.3 | 3.40 | 6.63 |
| Comparison: MoO$_2$(acac)$_2$* | 0.0322 | 45 | — | — | — | 6.05 |

*acac = acetylacetonate

2.2 Bulk Polymerization

Round-bottom flasks heated to 80° C. were charged with 6.804 g (75.6 mmol) of liquid trioxane and each admixed with one of the catalysts listed in Table 2. The time between addition of the catalyst and the onset of cloudiness was measured as the induction time. The reaction was then terminated by adding 50 ml of water. The polymer obtained was filtered off, washed with water and acetone, dried in a drying cabinet at 70° C. for from 1 to 2 h and its yield was determined. In the following table, the induction times, reaction times and yields are reported.

TABLE 2

| Run No. | Catalyst | Quantity [mmol] | Induction time [s] | Reaction time [min] | Yield [g] |
|---|---|---|---|---|---|
| 1 | I.1 | 0.0152 | 5–10 | 0.33 | 5.565 |
| 2 | I.1 | 0.0152 | 5–10 | 0.5 | 5.323 |
| 3 | I.5 | 0.0180 | 600 | 30 | 5.704 |

2.3 Polymerization in Solution in the Presence of Water

A solution of from 40 to 50% trioxane in 6 ml of formalin-saturated dichloroethane (water content: about 0.5% by volume) is mixed with 100 µl of 1,3-dioxepane and heated to 80° C. To each reaction mixture, a solution of one of the catalysts listed in Table 3 in 1 ml of dichloromethane is added in the appropriate quantity. The time between addition of the catalyst and the onset of cloudiness was measured as the induction time. After 4 h, the reaction was stopped by cooling the reaction mixture. The workup was effected as described in 2.1. In Table 3, the induction times measured and also the number average and weight average molar masses of the polyoxymethylene obtained, the polydispersity index (PDI=$M_w/M_n$) and the crude yields are reported.

TABLE 3

| Catalyst | Quantity [mmol] | Induction time [s] | $M_w$ [kg/mol] | $M_n$ [kg/mol] | PDI | Crude yield [g] |
|---|---|---|---|---|---|---|
| I.1 | 0.0353 | 10 | 10.0 | 3.3 | 3.0 | 2.61 |
| I.2 | 0.0313 | 50 | 9.1 | 2.8 | 3.25 | 2.82 |
| I.7 | 0.0296 | 10 | 20.5 | 9.6 | 2.14 | 2.73 |
| I.8 | 0.0104 | 21 | 11.6 | 4.9 | 2.37 | 2.19 |
| I.9 | 0.0284 | 15 | 13.8 | 7.1 | 1.94 | 1.55 |

TABLE 3-continued

| Catalyst | Quantity [mmol] | Induction time [s] | $M_w$ [kg/mol] | $M_n$ [kg/mol] | PDI | Crude yield [g] |
|---|---|---|---|---|---|---|
| Comparison: $MoO_2(acac)_2$* | 0.0293 | blue coloration after 1 min | — | — | — | — |

*acac = actylacetonate

As the comparison of the reactions using the catalysts according to the invention and the prior art $MoO_2(acac)_2$ shows, the catalysts according to the invention lead to higher yields. The catalytic activity of the catalysts according to the invention is further maintained even in the presence of water, in contrast to $MoO_2$ $(acac)_2$.

We claim:

1. A process for preparing polyoxymethylene by contacting a formaldehyde source with a catalyst of the formula I $$[Cp_vML_w]^{m+}Z_{m/n}^{n-} \quad (I)$$

where

M is Ti, Zr, Hf, V, Nb, Ta, Cr, Mo, W, Mn, Re, Fe, Ru, Os, Co, Rh or Ir,

Cp is a cyclopentadienyl ligand $C_5H_{(5-u)}R^1_u$, where
u is from 0 to 5 and
$R^1$ is alkyl, alkenyl, aryl, heteroaryl, aralkyl, $COOR^2$, $COR^2$, CN or $NO_2$, and
$R^2$ is H, alkyl, aryl or aralkyl, v is 1 or 2, each L is independently a nitrile, CO or a ligand displaceable by CO, w is an integer from 0 to 4, Z is an anion, and m and n are each independently an integer from 1 to 3.

2. A process as claimed in claim 1 where
Cp is a cyclopentadienyl ligand $C_5H_{(5-u)}R^1_u$, where
$R^1$ is methyl, CHO, $COCH_3$, $COC_2H_5$, $COOCH_3$, $COOC_2H_5$, CN or $NO_2$.

3. A process as claimed in claim 1 where M is Mo or W.

4. A process as claimed in claim 1 where each L is selected independently from nitriles, CO, alkenes, phosphines, amines, ethers, carboxylic esters, cyclic carbonic esters, epoxides, hemiacetals, acetals and nitro compounds.

5. A process as claimed in claim 1 where Z is a halide, sulfonate of the formula $OSO_2R$, where R is alkyl, partially or fully halogenated alkyl or aryl, carboxylate, complexed borate, complexed phosphate, complexed arsenate or complexed antimonate.

6. A process as claimed in claim 5 where Z is chloride, acetate, trifluoroacetate or trifluoromethanesulfonate.

7. A process as claimed in claim 1 where the formaldehyde source is formaldehyde, trioxane or paraformaldehyde.

8. A catalyst of the formula Ia $$[CpM(CO)_2)L]^+Z_{1/n}^{n-} \quad (Ia)$$

where

M is Mo or W,

Cp is a cyclopentadienyl ligand $C_5H_4R^1$ or $C_5H_3R^1_2$, where $R^1$ is CHO, $COCH_3$, $COOCH_3$ or $COOC_2H_5$, L is CO or $CH_3CN$, Z is trifluoromethanesulfonate, trifluoroacetate, tetrafluoroborate, hexafluorophosphate or hexafluoroantimonate and n is an integer from 1 to 3.

9. A catalyst as claimed in claim 8 where
Cp is a cyclopentadienyl ligand $C_5H_4R^1$ where $R^1$ is CHO, $COCH_3$ or $COOCH_3$ or is a cyclopentadienyl ligand $C_5H_3R^1_2$ where $R^1$ is $COOC_2H_5$.

* * * * *